(12) United States Patent
Swanson (10) Patent No.: US 8,831,744 B2
(45) Date of Patent: Sep. 9, 2014

(54) STIMULATION LEAD COMPRISING INTERNAL FLEX FILM COMPONENT AND METHOD OF FABRICATION

(71) Applicant: Advanced Neuromodulation Systems, Inc., Plano, TX (US)

(72) Inventor: John Swanson, Lake Oswego, OR (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 0 days.

(21) Appl. No.: 13/873,010

(22) Filed: Apr. 29, 2013

(65) Prior Publication Data

US 2013/0312258 A1    Nov. 28, 2013

Related U.S. Application Data

(63) Continuation of application No. 13/070,055, filed on Mar. 23, 2011, now abandoned.

(60) Provisional application No. 61/316,546, filed on Mar. 23, 2010.

(51) Int. Cl.
*A61N 1/00* (2006.01)
*A61N 1/05* (2006.01)
*H01R 13/66* (2006.01)
*H01R 24/58* (2011.01)

(52) U.S. Cl.
CPC .............. *A61N 1/05* (2013.01); *A61N 1/0551* (2013.01); *H01R 13/6658* (2013.01); *H01R 24/58* (2013.01); *A61N 1/0553* (2013.01); *H01R 2201/12* (2013.01)
USPC .............................................. 607/116; 29/746

(58) Field of Classification Search
CPC ...... A61N 1/05; A61N 1/0553; A01B 18/1492
USPC .............................................. 607/116; 29/746
See application file for complete search history.

(56) References Cited

U.S. PATENT DOCUMENTS

| | | | | |
|---|---|---|---|---|
| 2004/0127968 A1* | 7/2004 | Kuzma et al. | ................. | 607/137 |
| 2005/0027338 A1* | 2/2005 | Hill | ................. | 607/116 |
| 2006/0265037 A1* | 11/2006 | Kuzma | ................. | 607/116 |

* cited by examiner

*Primary Examiner* — Christopher D Koharski
*Assistant Examiner* — Philip Edwards (57) ABSTRACT

In one embodiment, a stimulation lead for applying electrical pulses to tissue of a patient, the stimulation lead comprises: a plurality of electrodes on a first end of the lead body; a plurality of terminals on a second end of the lead body; a lead body comprising a flex film component disposed within insulative material, wherein (i) the flex film component comprises a plurality of electrical traces, (ii) the plurality of electrical traces electrically couple the plurality of electrodes with the plurality of terminals, and (iii) the flex film component comprises a plurality of bends along a substantial length of the lead body; wherein the stimulation lead is adapted to elastically elongate under application of stretching forces to the lead body without disconnection of the electrical connections between the plurality of electrodes and the plurality of terminals through the electrical traces of the flex film component.

10 Claims, 6 Drawing Sheets

STIMULATION LEAD COMPRISING INTERNAL FLEX FILM COMPONENT AND METHOD OF FABRICATION

CROSS-REFERENCE TO RELATED APPLICATIONS

This application is a continuation of U.S. patent application Ser. No. 13/070,055, filed Mar. 23, 2011, which claims the benefit of U.S. Provisional Application No. 61/316,546, filed Mar. 23, 2010, which is incorporated herein by reference.

TECHNICAL FIELD

This application is generally related to implantable stimulation lead for application of electrical pulses to tissue of a patient and methods of fabrication.

BACKGROUND

Neurostimulation systems are devices that generate electrical pulses and deliver the pulses to nerve tissue to treat a variety of disorders. Spinal cord stimulation (SCS) is the most common type of neurostimulation. In SCS, electrical pulses are delivered to nerve tissue in the spine typically for the purpose of chronic pain control. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals, which are also electrically coupled to the wire conductors, that are adapted to receive electrical pulses. The distal end of a respective stimulation lead is implanted within the epidural space to deliver the electrical pulses to the appropriate nerve tissue within the spinal cord that corresponds to the dermatome(s) in which the patient experiences chronic pain. The stimulation leads are then tunneled to another location within the patient's body to be electrically connected with a pulse generator or, alternatively, to an "extension."

The pulse generator is typically implanted within a subcutaneous pocket created during the implantation procedure. In SCS, the subcutaneous pocket is typically disposed in a lower back region, although subclavicular implantations and lower abdominal implantations are commonly employed for other types of neuromodulation therapies.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

Known techniques for fabrication of lead bodies involve providing multiple conductors within insulative material. The conductors may be helically wrapped in a controlled manner. Alternatively, the conductors may be arranged in a linear manner along the length of the lead body. Extrusion techniques may be employed to provide the insulative material. Additionally or alternatively, an outer sheath of insulative material may be provided over the conductors. Despite the differences in different fabrication techniques, known fabrication techniques are adapted to cause the lead body to be sufficiently robust to withstand repetitive flexing in the human body over a long period of time. Such known techniques can be relatively complex, time consuming, and expensive.

SUMMARY

In one embodiment, a stimulation lead for applying electrical pulses to tissue of a patient, the stimulation lead comprises: a plurality of electrodes on a first end of the lead body; a plurality of terminals on a second end of the lead body; a lead body comprising a flex film component disposed within insulative material, wherein (i) the flex film component comprises a plurality of electrical traces, (ii) the plurality of electrical traces electrically couple the plurality of electrodes with the plurality of terminals, and (iii) the flex film component comprises a plurality of bends along a substantial length or a majority of the lead body; wherein the stimulation lead is adapted to elastically elongate under application of stretching forces to the lead body without disconnection of the electrical connections between the plurality of electrodes and the plurality of terminals through the electrical traces of the flex film component.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

Figures 1, 2A, 2B, 2C:
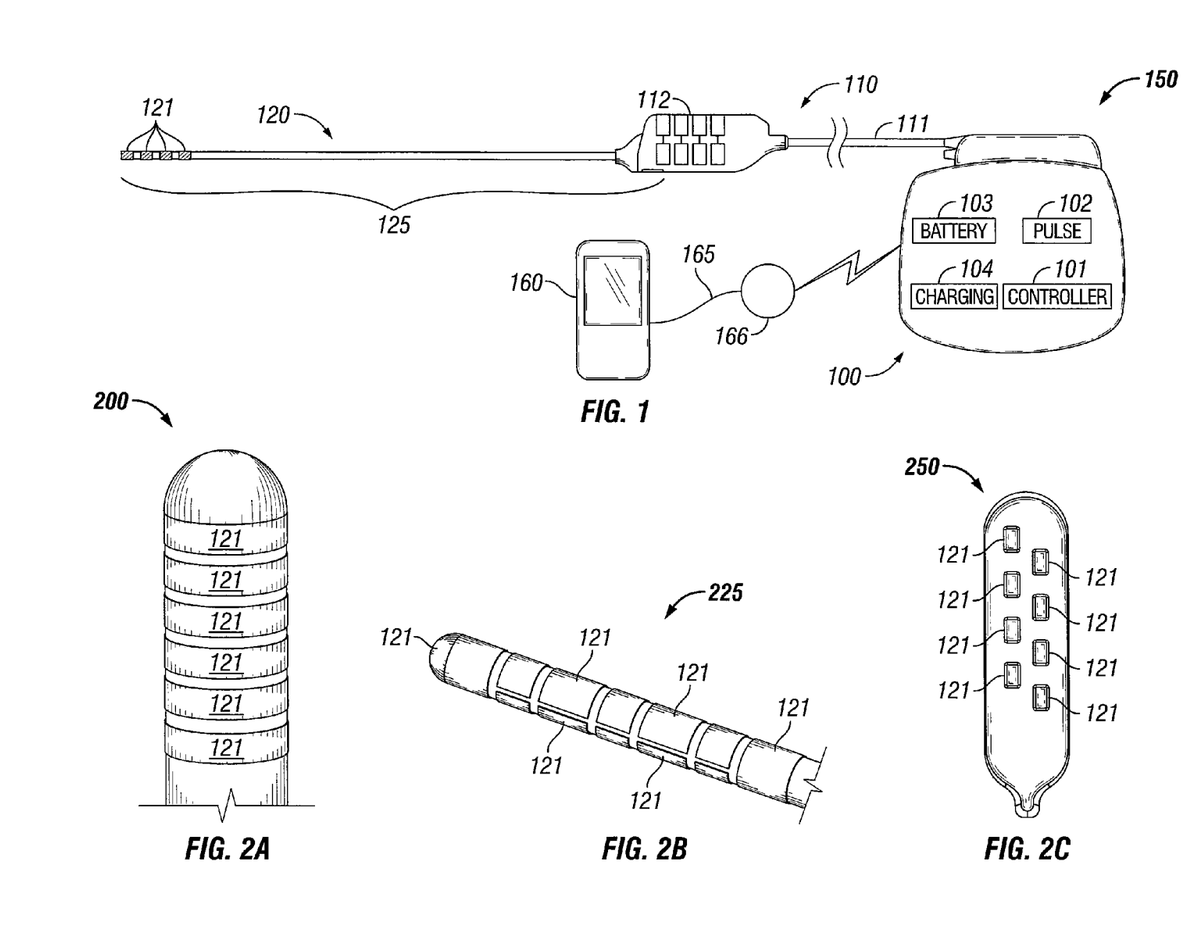
FIG. 1 depicts a stimulation system according to one representative embodiment.
FIGS. 2A-2C respectively depict stimulation portions for inclusion at the distal end of lead according to some representative embodiments.

FIG. 1 depicts stimulation system 150 that generates electrical pulses for application to tissue of a patient according to one embodiment. In one embodiment, system 150 is adapted to generate electrical pulses and deliver the pulses to tissue of the patient. For example, system 150 may be adapted to stimulate spinal cord tissue, peripheral nerve tissue, deep brain tissue, cortical tissue, cardiac tissue, digestive tissue, pelvic floor tissue, or any other suitable tissue within a patient's body.

System 150 includes implantable pulse generator 100 that is adapted to generate electrical pulses for application to tissue of a patient. Implantable pulse generator 100 typically comprises a metallic housing that encloses pulse generating circuitry 102, controller 101, charging coil (not shown), battery 103, far-field and/or near field communication circuitry (not shown), battery charging circuitry 104, etc. of the device. Although an implantable pulse generator is shown for the embodiment of FIG. 1, an external pulse generator (e.g., a "trial" stimulator) may alternatively be employed. The controller 101 typically includes a microcontroller or other suitable processor for controlling the various other components of the device. Software code is typically stored in memory of the pulse generator 100 for execution by the microcontroller or processor to control the various components of the device.

A processor and associated charge control circuitry for an implantable pulse generator is described in U.S. Patent Publication No. 20060259098, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. patent Ser. No. 11/109,114, entitled "IMPLANTABLE DEVICE AND SYSTEM FOR WIRELESS COMMUNICATION," which is incorporated herein by reference. Examples of commercially available implantable pulse generators and related devices include the EON™ MINI pulse generator, RAPID PROGRAMMER™ system, and patient controller devices available from St. Jude Medical Neuromodulation (Plano, Tex.), the PRECISION PLUS™ SCS System (including pulse generator, cordless charger, programmer with I-SCULPT™, and patient "Remote Control") available from Boston Scientific Neuromodulation Corporation (Valencia, Calif.), and the RESTOREULTRA™ neurostimulator, N'VISION™ Clinician Programmer, MYSTIM™ Patient Programmer and available from Medtronic, Inc. (Minneapolis, Minn.). Stimulation leads according to some representative embodiment may be adapted to connect and/or otherwise function with any of these commercially available devices directly and/or through the use of an "extension" or "adapter" (such as the OMG™ adapter from Boston Scientific Neuromodulation).

An example and discussion of "constant current" pulse generating circuitry is provided in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within pulse generator 100. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation system 150 further comprises one or more stimulation leads 120. Stimulation lead(s) 120 may be intended for long-term implantation or for short-term "trial" use as known in the art. Stimulation lead 120 comprises a lead body of insulative material about a plurality of conductors that extend from a proximal end of lead 120 to its distal end. The conductors electrically couple a plurality of electrodes 121 to a plurality of terminals (not shown) of lead 120. The terminals are adapted to receive electrical pulses and the electrodes 121 are adapted to apply stimulation pulses to tissue of the patient. Also, sensing of physiological signals may occur through electrodes 121, the conductors, and the terminals. Additionally or alternatively, various sensors (not shown) may be located near the distal end of stimulation lead 120 and electrically coupled to terminals through conductors within the lead body 111.

FIGS. 2A-2C respectively depict stimulation portions 200, 225, and 250 for inclusion at the distal end of lead 120. Stimulation portion 200 depicts a conventional stimulation portion of a "percutaneous" lead with multiple ring electrodes. Stimulation portion 225 depicts a stimulation portion including several "segmented electrodes." The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. Provisional Patent Application Ser. No. 61/247,360, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure.

Stimulation system 150 optionally comprises extension lead 110. Extension lead 110 is adapted to connect between pulse generator 100 and stimulation lead 120. That is, electrical pulses are generated by pulse generator 100 and provided to extension lead 110 via a plurality of terminals (not shown) on the proximal end of extension lead 110. The electrical pulses are conducted through conductors within lead body 111 to housing 112. Housing 112 includes a plurality of electrical connectors (e.g., "Bal-Seal" connectors) that are adapted to connect to the terminals of lead 120. Thereby, the pulses originating from pulse generator 100 and conducted through the conductors of lead body 111 are provided to stimulation lead 120. The pulses are then conducted through the conductors of lead 120 and applied to tissue of a patient via electrodes 121.

In practice, stimulation lead 120 is implanted within a suitable location within a patient adjacent to tissue of a patient to treat the patient's particular disorder(s). The lead body extends away from the implant site and is, eventually, tunneled underneath the skin to a secondary location. Housing 112 of extension lead 110 is coupled to the terminals of lead 120 at the secondary location and is implanted at that secondary location. Lead body 111 of extension lead 110 is tunneled to a third location for connection with pulse generator 100 (which is implanted at the third location). For "trial" stimulation. the terminal end of lead 120 is left external to the patient's body and is coupled to the connector portion of an external pulse generator as is known in the art.

Controller device 160 may be implemented to recharge battery 103 of pulse generator 100 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery 103 by charging circuitry 104. Charging circuitry 104 may also communicate status messages to controller 160 during charging operations using pulse-loading or any other suitable technique. For example, controller 160 may communicate the coupling status, charging status, charge completion status, etc.

External controller device 160 is also a device that permits the operations of pulse generator 100 to be controlled by user after pulse generator 100 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 100.

Controller device 160 preferably provides one or more user interfaces to allow the user to operate pulse generator 100 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. IPG 100 modifies its internal parameters in response to the control signals from controller device 160 to vary the stimulation characteristics of stimulation pulses transmitted through stimulation lead 120 to the tissue of the patient. Neurostimulation systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

Figure 3:
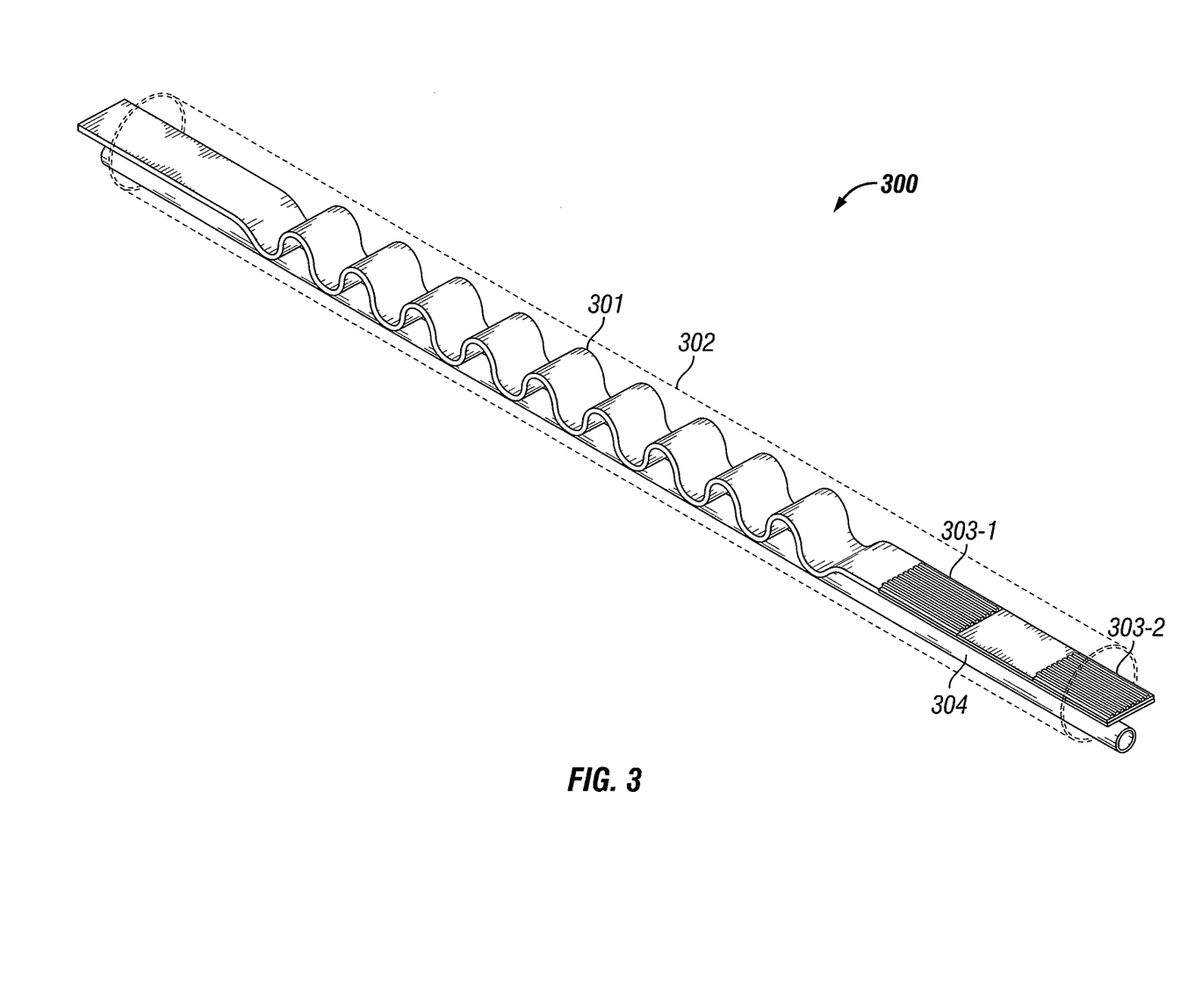
FIG. 3 depicts a lead body including an internal flex film component according to one representative embodiment.

In some embodiments, stimulation lead 120 is fabricated using an internal flex film component. FIG. 3 depicts stimulation lead body 300 according to one representative embodiment. Stimulation lead body 300 comprises flex film component 301 within insulative material 302. Flex film component 301 includes a plurality of conductive traces sealed within the flex film material (e.g., liquid crystal polymer (LCP)).

In one embodiment, two layers of flex film are included within flex film component 301 and two respective sets 303-1 and 303-2 of conductive traces are provided. In this specific embodiment, eight conductive traces are provided for each layer within the LCP material. In one embodiment, each conductor trace is 50 microns wide and 18 microns thick. In a respective layer of flex film component 301, respective conductor traces are separated by a 50 micron pitch. Suitable materials for conductor traces include copper, gold, platinum, platinum/iridium traces, and/or the like. The conductive traces extend along the length of lead body 300 for the purposes of conducting stimulating current along the length of lead body 300 between electrodes and terminals. The distal ends of the two sets 303-1 and 303-2 of conductive traces are shown to be exposed for the sake of illustration. Flex film component 301 may be fabricated using conventional processes. Although LCP is employed according to one representative embodiment, other suitable flexible polymer materials may be employed such as polyimide.

As shown in FIG. 3, flex film component 301 is provided with a serpentine configuration within lead body 300. That is, flex film component 301 is sinuous, bending "up" and "down" in respective curves repeatedly along the length of lead body 300. This sinuous or serpentine portion preferably substantially extends between the distal and proximal portions. In another embodiment, the sinuous or serpentine portion or portions cover a majority of the length of lead body 300. When a stretching force is applied to lead body 300, flex film component 301 is capable of elastic elongation. That is, lead body 300 will increase its length under the stretching force by reducing the curvature in the bends of flex film component 301. When the stretching force is removed, flex film component 301 returns to its prior configuration.

Figure 6:
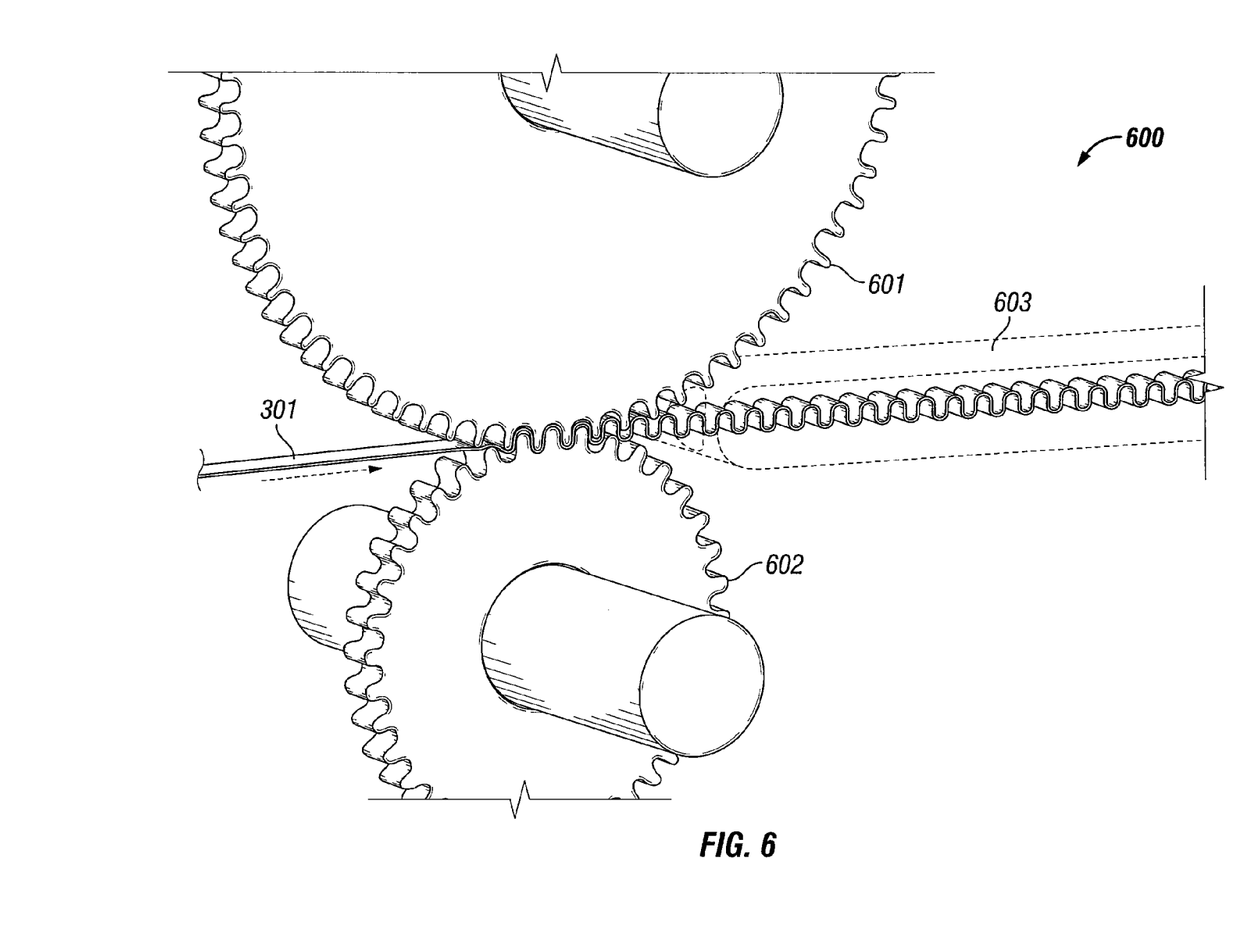
FIGS. 6 and 7 depict two devices for providing a serpentine shape to a flex film for inclusion within a stimulation lead according to respective embodiments.

FIG. 6 depicts device 600 for providing a serpentine shape to flex film component 301. Device 600 comprises two opposing gears 601 and 602 which are driven by respective drive elements (not shown). The planar flex film is drawn into gears 601 and 602. Further, one or more of gears 601 and 602 are heated which, in turn, causes flex film component 301 to be heated (e.g., above its glass transition temperature) to assist shaping flex film component 301. Device 600 further comprises cooling vent 603 to vent cool air onto flex film component 301 upon exiting gears 601 and 602 to set the serpentine shape.

Figure 7:
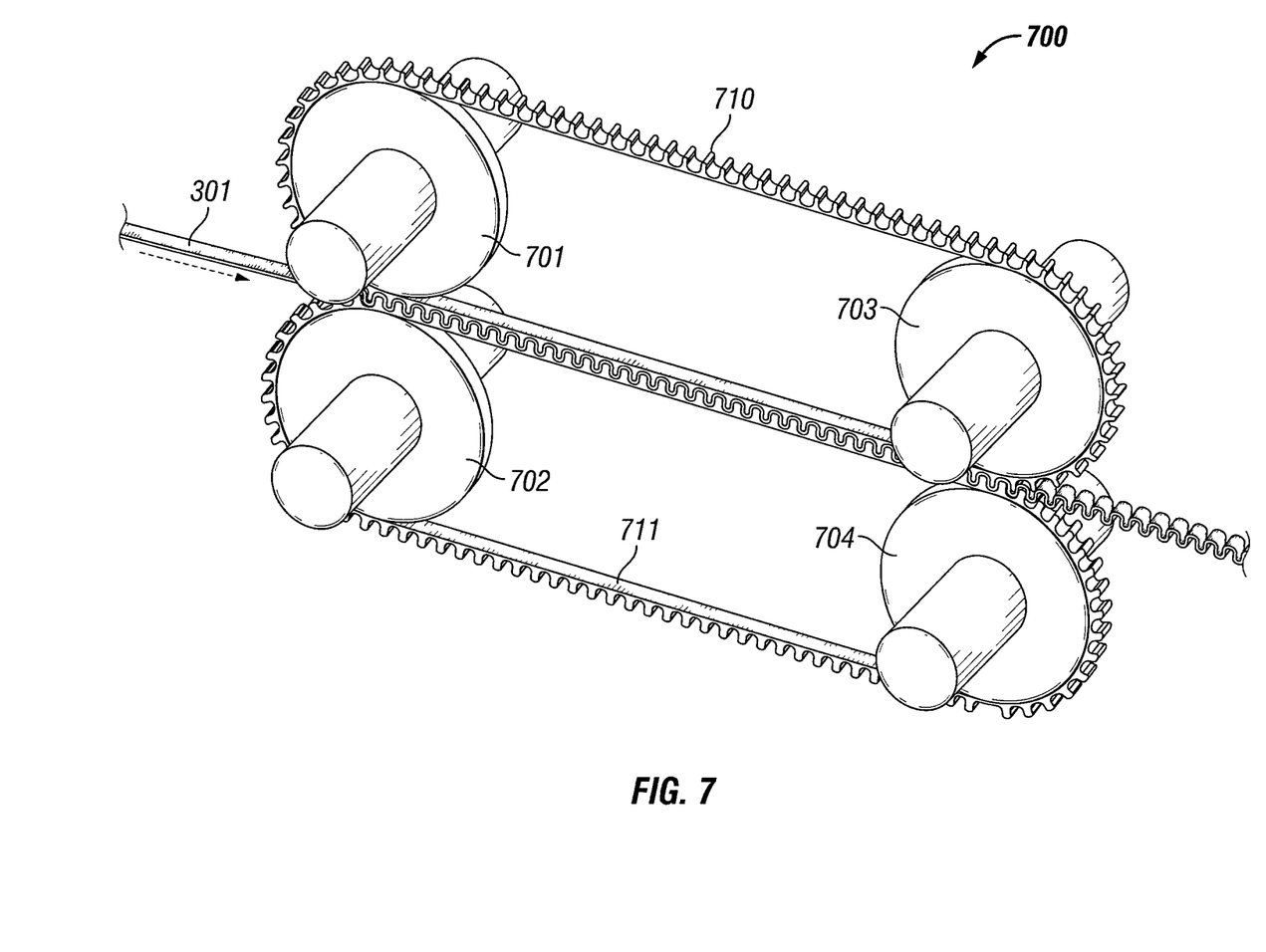

FIG. 7 depicts device 700 for providing a serpentine shape to flex film component 301. Device 700 comprises a first set of gears 701 and 702 and a second set of gears 703 and 704, which are driven by respective drive elements (not shown). In the embodiment shown in FIG. 7, gears 701-704 drive belts 710 and 711 about gears 701-704. Belt 710 is driven by gears 701 and 703 while belt 711 is driven by gears 702 and 704. Belts 710 and 711 may be fabricated using a suitable metal, plastic, or glass fiber materials according to some representative embodiments. Belts 710 and 711 includes indentations that correspond to the desired serpentine shape. Flex film component 301 is initially drawn between belts 710 and 711 and through gears 701 and 702. One or more of gears 701 and 702 are heated which, in turn, causes flex film component 301 to be heated (e.g., above its glass transition temperature) to assist shaping flex film component 301. Flex film component 301 is then cooled to set the serpentine shape as flex film component proceeds through gears 703 and 704.

Referring again to FIG. 3, stimulation lead body 300 comprises elastic tube 304 Elastic tube 304 preferably provides a low friction surface to ease insertion and removal of a stiffening/steering stylet through lead body 300. In one embodiment, elastic tube 304 possess an inner diameter of approximately 0.020 inches. Also, elastic tube 304 is adapted to flex and elongate. A suitable material for elastic tube 304 is CARBOSIL™ (a silicone polycarbonate urethane) or CarobSil-F (a fluorinated silicone polycarbonate urethane).

Insulative material 302, surrounding flex film component 301 and elastic tube 304, is likewise capable of elastic elongation by suitably selecting material characteristics of material 302. A relatively low durometer may be selected for material 302, for example, at approximately or below a durometer of 40 shore A.

Fabrication of stimulation lead body 300 may occur using different combinations of processing steps. In some embodiments, the process begins by fabricating elastic tube 304. In one embodiment, a TEFLON™-coated mandrel is coated with suitable elastic, biocompatible insulative material. The coated-mandrel is cut to length. A length of flex film component 301 with embedded conductive traces is fabricated. Any suitable length may be employed for tube 304 and flex film component 301. For example, in one embodiment, tube 304 and flex film component 301 in their non-stretched or relaxed states are fabricated to be approximately 30 cm. When component 301 is adapted to include multiple layers, the layers are fabricated in a "stair-stepped" manner at the ends of component 301 to facilitate access to each layer. The medial portion of flex film component 301 is fabricated or post-fabrication processed to repeatedly bend back and forth along the length of component 301 while the respective ends of flex film component 301 are preferably left substantially flat. As can be appreciated, the leads may also be fabricated in a continuous process to offer improvements in productivity.

Upon fabrication of these components, flex film component 301 and tube 304 are adhered together. Insulative material 302 is provided over the assembly of flex film component 301 and tube 304. Any suitable process may be employed to provide insulative material 302 including dip-coating, spraying, over-molding, etc. Centerless grinding or other mechanical processing may be applied to obtain a substantially uniform outer diameter. In one embodiment, an outer diameter of lead body 300 of 0.060 inches is obtained, although any suitable diameter may be selected.

By fabricating lead body 300 in the discussed manner, lead body 300 is capable of elastic elongation under relatively low stretching forces. Also, after removal of the stretching force, lead body 300 is capable of resuming its original length and profile. For example, lead body 300 may stretch 10%, 20%, 25%, 35%, or even up or above to 50% at forces of about 0.5, 1.0, and/or 2.0 pounds of stretching force. The ability to elongate at relatively low forces may present one or more advantages for implantation in a patient. For example, as a patient changes posture (e.g., "bends" the patient's back), the distance from the implanted pulse generator to the stimulation target location changes. Lead body 300 may elongate in response to such changes in posture without damaging the conductors of lead body 300 or disconnecting from pulse generator. Also, deep brain stimulation implants, cortical stimulation implants, and occipital subcutaneous stimulation implants usually involve tunneling of the lead body through tissue of the patient's neck to a location below the clavicle. Movement of the patient's neck subjects a stimulation lead to significant flexing and twisting which may damage the conductors of the lead body. Due to the ability to elastically elongate, lead body 300 is better adapted for such implants than some other lead body designs.

After fabrication of lead body 300, electrodes and terminals are provided on lead body 300 to form a functional stimulation lead 120. The respective layers of flex film component 301 are preferably arranged to facilitate electrode and terminal fabrication. As shown in FIG. 3, the conductive traces 303-2 of the "lower" layer of flex film component 301 extend beyond the conductive traces 303-1 of the "upper" layer of flex film component 301. Thereby, traces 303-2 are readily accessible for subsequent electrical connection with other electrical components.

Figure 4:
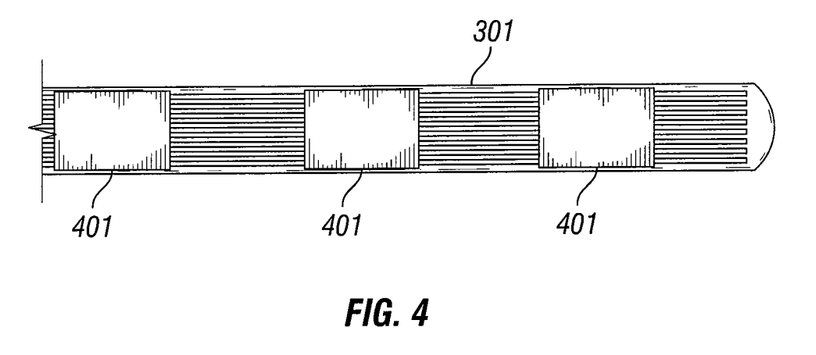
FIG. 4 depicts a segment of a flex film component including bond pads according to one representative embodiment.

Further, in one embodiment, as shown in isolation in FIG. 4, a respective bond or connection pad 401 is fabricated on the upper surface of flex film component 301. Each pad 401 is electrically connected to one of the electrical traces of sets 303-1 and 303-2 of traces. Although only one end of flex film component 301 is shown in FIG. 4, sets of pads 401 are preferably provided on each end of flex film component 301 for subsequent electrical connection with electrodes and terminals.

Figure 5:
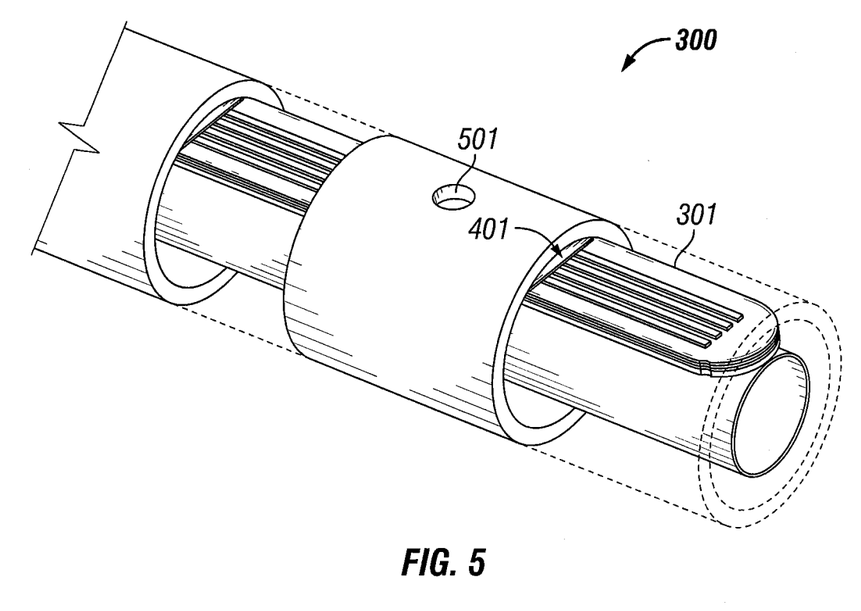
FIG. 5 depicts electrodes on a distal end of a stimulation lead body according to one representative embodiment.

FIG. 5 depicts provision of one electrode at the distal end of lead body 300 (terminals may be fabricated in the same manner on the opposite end of lead body 300). As shown in FIG. 5, via 501 is provided to electrically connect to one of the bond pads 401. A suitable laser may be employed to ablate insulative material 302 of lead body to expose the respective bond pad 401. Conductive material is provided within the created aperture to form via 501. Electrode 502 is provided in electrical contact with via 501.

A number of suitable techniques may be employed for this process (see electrode attachment techniques disclosed in U.S. Pat. No. 7,039,470, entitled "Medical lead and method for medical lead manufacture," which is incorporated herein by reference). In one embodiment, a jumper wire is utilized to connect to bond pad 401 through an aperture in lead body 300. The jumper wire is welded to the conductive band placed about the lead body 300. Crimping or swaging of the conductive band may be employed to place the conductive band about the lead body.

In one embodiment, electrode 502 is fabricated using a liquid dispensing process. For example, a conductive polymer in a suitable solvent may be disposed about the circumference of lead body 300. During the dispensing process, the conductive polymer fills the aperture in lead body 300 and forms a conductive ring at the appropriate axial position along lead body 300. After application of the conductive polymer, plating of conductive material (e.g., platinum) may also be employed to form electrode 502. Also, another conductive polymer material (e.g., a PEDOT-based conductive polymer material) may be employed over the initial dispensed material.

In other embodiments, a paddle style distal end with an array of electrodes may be provided. Each electrode may be electrically coupled to a respective conductive trace of flex film component 301 through a respective bond pad 401 and a respective jumper wire. In another embodiment, segmented electrodes may be fabricated in lieu of circumferential electrodes.

In one embodiment, the terminal end (not shown) may be fabricated to include a bifurcated structure. In such an embodiment, the lower layer and corresponding conductive traces 303-2 may be split from the upper layer and corresponding traces 303-1 of flex film component 301 which are each encapsulated or enclosed within separate sections of insulative material 302. Two separate sets of terminals may then be provided in electrical connection with respective bond pads for each of the separate layers of flex film component 301. Bifurcation at the terminal end may be appropriate to adapt the stimulation lead 120 for conventional pulse generator header designs (e.g., two separate sets of eight "Bal-Seal" connectors).

Figure 8A:
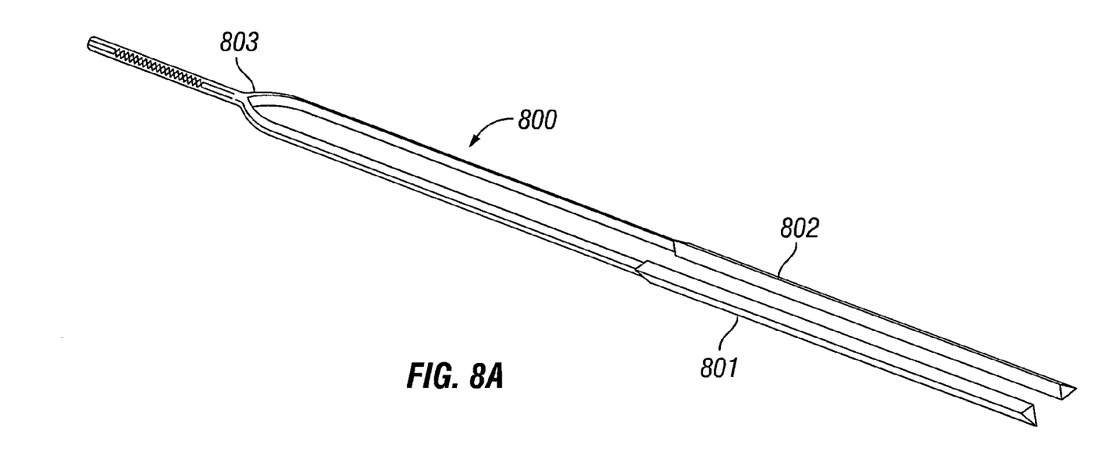
FIGS. 8A and 8B depicts a bifurcated terminal portion of a stimulation lead in two different configurations according to one representative embodiment.
Figure 8B:
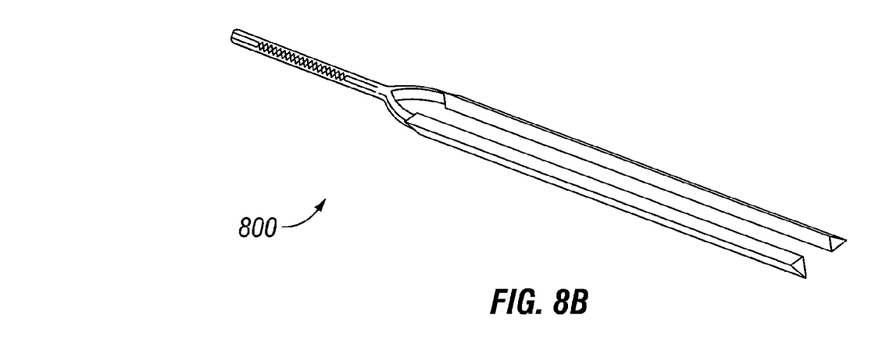

FIGS. 8A and 8B depicts bifurcated terminal end 800 of a stimulation lead in two different configurations according to one representative embodiment. Terminal end 800 comprises two separated terminal portions 801 and 802. As discussed above, the flex film component is split into two separate portions which are enclosed within terminal portions 801 and 802, respectively. Terminal portions 801 and 802 may be fabricated using PEEK and CARBOSIL® materials including suitable conductor materials to connect to the terminals (not shown). Terminal portions 801 and 802 are rounded on one side and are substantially flat on the other side. Entry point 803 is provided between terminal portions 801 and 802 to permit the surgeon to insert a guide wire or stylet into the stimulation lead.

Further, terminal portions 801 and 802 are foldable. In FIG. 8A, terminal portions 801 and 802 are shown fully extended. In FIG. 8B, terminal portions 801 and 802 are folded upon themselves thereby following substantially round cross-sections. In the folded configuration, terminal portions 801 and 802 substantially conform to the dimensions of conventional stimulation leads. For example, in the configuration shown in FIG. 8B, terminal portions 801 and 802 may be inserted within respective header apertures of an implantable pulse generator (e.g., an EON® MINI pulse generator). In the configuration shown in FIG. 8A, by extending terminal portions 801 and 802, terminal portions 801 and 802 may be passed through a conventionally sized needle used for epidural implants.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A method of fabricating a stimulation lead for applying electrical pulses to tissues of a patient, the method comprising:
providing a flex film component, the flex film component being an elongated planar strip having a top planar surface and a bottom planar surface, the flex film component further that includes a first plurality of electrical traces extending from a proximal portion to a distal portion of the flex film component;
shaping the flex film component to comprise a plurality of bends along a substantial length of the lead body;
enclosing the flex film component in an elastic insulative material to form a lead body;
providing a plurality of electrodes on a first end of the lead body;
providing a plurality of terminals on a second end of the lead body, wherein the plurality of electrodes are electrically coupled to the plurality of terminals through the first plurality of electrical traces of the flex film component,
wherein the stimulation lead is adapted to elastically elongate under application of stretching forces to the lead body without disconnection of the electrical connections between the plurality of electrodes and the plurality of terminals through the first plurality of electrical traces of the flex film component.

2. The method of claim 1 wherein the shaping comprises:
directing the flex film component through a plurality of gears to form a serpentine shape in the flex film component.

3. The method of claim 2 wherein at least one of the plurality of gears heats the flex film component.

4. The method of claim 3 wherein the flex film component is heated above its glass transition temperature.

5. The method of claim 3 further comprising:
directly cooling the flex film component after shaping the flex film component with the at least one gear of the plurality of gears employed for heating the flex film component.

6. The method of claim 5 wherein the cooling comprising:
operating one or more vents to providing cooling air over the flex film component upon exiting from the at least one gear.

7. The method of claim 1 wherein the flex film component comprises a plurality of conductive pads that each electrically interconnect one of the first plurality of electrical traces and with a respective one of the plurality of electrodes and terminals.

8. The method of claim 7 wherein the stimulation lead further comprises a plurality of vias, disposed underneath the plurality of electrodes and the plurality of terminals, electrically connected with the plurality of conductive pads.

9. The method of claim 1 wherein the shaping leaves a flat first end and flat second end in sections of the flex film component proximate to the plurality of electrodes and the plurality of terminals, respectively.

10. The method of claim 1 wherein a second plurality of electrical traces extend past the first plurality of electrical traces at a first end and at a second end of the flex film component.

* * * * *